US005741935A

United States Patent [19]

Bowden et al.

[11] Patent Number: 5,741,935
[45] Date of Patent: Apr. 21, 1998

[54] PREPARATION OF ORGANIC PENTAFLUOROSULPHUR COMPOUNDS

[75] Inventors: Roy D. Bowden; Martin P. Greenhall; John S. Moilliet; Julie Thomson, all of Preston, Great Britain

[73] Assignee: British Nuclear Fuels plc, Cheshire, Great Britain

[21] Appl. No.: 809,771

[22] PCT Filed: Jul. 26, 1996

[86] PCT No.: PCT/GB96/01829

§ 371 Date: Apr. 9, 1997

§ 102(e) Date: Apr. 9, 1997

[87] PCT Pub. No.: WO97/05106

PCT Pub. Date: Feb. 13, 1997

[30] Foreign Application Priority Data

Jul. 29, 1995 [GB] United Kingdom ............... 9515599

[51] Int. Cl.[6] .................................................. C07C 381/00
[52] U.S. Cl. ............................................................. 568/74
[58] Field of Search ................................................ 568/74

[56] References Cited

U.S. PATENT DOCUMENTS 522,070   6/1894   St. Clair .
3,102,903  9/1963   Coffman .
3,117,158  1/1964   Sheppard .

FOREIGN PATENT DOCUMENTS 682749    3/1964   Canada .
94/22817  10/1994  WIPO .
WO94/22817 10/1994 WIPO .

OTHER PUBLICATIONS

"Novel Synthesis of Unusual Classes of Fluorocarbon Organosulfur Compounds Using Elemental Fluorine as a Reagent" by Huang ett al., Inorganic Chemistry, vol. 30, No. 4, Feb. 20, 1991, pp. 789–794.

"Sulfur Cyanide Pentafluoride $SF_5CN$" by Losking et al., Angewandte Chemie. International Edition, vol. 28, No. 9, Sep. 1989, pp. 1255–1256.

"Arylsulfur Pentafluorides" by Sheppard, Journal of the American Chemical Society, vol. 84, No. 16, Aug. 20, 1962, pp. 3064–3072.

*Primary Examiner*—C. Warren Ivy
*Assistant Examiner*—Jean F. Vollano
*Attorney, Agent, or Firm*—Sheridan Ross P.C.

[57] ABSTRACT

A process for the preparation of organic pentafluorosulphur compounds which comprises reacting an organic disulphide in a substantially inert solvent with elemental fluorine.

10 Claims, No Drawings

PREPARATION OF ORGANIC PENTAFLUOROSULPHUR COMPOUNDS

The present invention relates to the preparation of fluorinated organic compounds, in particular organic sulphur pentafluorides.

Organic sulphur pentafluorides such as arylsulphur pentafluorides are potentially important compounds useful, for example, in the manufacture of agricultural and pharmaceutical chemicals and polymer products. Convenient routes to these stable compounds are not generally available in the prior art because of the difficulty of making these compounds. Several examples of fluorination have been reported using silver (II) fluoride which is an expensive reagent. In many cases the yield has been very low. (Ref W A Sheppard J.A.C.S. 84 3058 (1962) Ibid 84 3064 (1962).

According to the present invention there is provided a method for the preparation of a pentafluoride having a formula (1) as follows:

$$R^1SF_5 \qquad (1)$$

wherein $R^1$ is as defined below, which comprises the step of converting into the compound of formula (1) a disulphide of formula (2) as follows:

$$R^1—S—S—R^2 \qquad (2)$$

wherein $R^2$ is as defined below, by reaction in a substantially inert solvent of the compound of formula (2) with elemental fluorine.

The groups $R^1$ and $R^2$ are independently selected from aryl, heteroaryl and aliphatic and alicyclic groups. Preferably $R^1$ and $R^2$ are the same although they may also be different groups where $R^1$ and $R^2$ are different, the product $R^1SF_5$ is present as a mixture with the corresponding product $R^2SF_5$.

Where $R^1$ and/or $R^2$ is aryl it may comprise an optionally substituted phenyl, biphenyl or naphthyl group.

Where $R^1$ and/or $R^2$ is heteroaryl it may comprise an optionally substituted mono- or bicyclic group containing one or more heteroatoms selected from nitrogen and oxygen. For example, $R^1$ and/or $R^2$ may be pyridyl, pyrimidyl or bipyridyl, quinoline and isoquinoline.

Where $R^1$ and/or $R^2$ is aliphatic or alicyclic it may be selected from optionally substituted alkyl or cycloalkyl groups eg having from 1 to 10 carbon atoms, especially 1 to 6 carbon atoms.

Where the group $R^1$ or $R^2$ is a substituted aryl group it may include from one to five substituents, eg especially one or two substituents, which are less reactive than the disulphide toward fluorine and which do not react with the organic sulphur trifluorides (formed during the conversion of compounds of formula (2) to those of formula (1)). Such substituent(s) may be selected from cyano, nitro, halogen, alkyl, fluoroalkyl, aryl, alkoxy and cycloalkyl.

A preferred form of the compound of formula (2) for use in the method of the present invention is $Ar^1$—S—S—$Ar^1$ wherein the $Ar^1$ groups are the same. Each $Ar^1$ may be a mono- or hi-cyclic aromatic ring optionally containing one or more substituents or heteroatoms. $Ar^1$ and $Ar^2$ may for example both be selected from phenyl, 4-nitrophenyl, 4cyanophenyl, 4-halophenyl.

The compound of formula (2) may in some examples be obtained by oxidation of a thiol of formula (3) as follows:

$$R^1—SH \qquad (3)$$

The thiol of formula (3) may be converted into the disulphide of formula (2) by use of fluorine in the fluorination step. Thus, the thiol of formula (3) may be used as the starting material in a reaction in which the compound of formula (2) is produced during reaction with elemental fluorine.

In the process according to the present invention, the compound of formula (2) may be contained in an inert solvent which is substantially anhydrous and aprotic. Suitable solvents include organic liquids which do not contain compounds having hydroxyl or carbonyl groups, eg solvents selected from acetonitrile, chlorinated or fluorinated hydrocarbons or perfluorocarbons or mixtures of them.

The process according to the present invention may be carried out by passing fluorine gas into a slurry or solution of the compound of formula (2) in the solvent medium. The reaction may be carried out by passing the fluorine into a vessel in which the slurry or solution is present or, alternatively, a flowstream of the slurry or solution may be contacted by the fluorine gas in co- or counter-current fashion.

The process according to the present invention may be carried out at a temperature in the range −40° C. to 40° C., especially −20° C. to 25° C. A temperature in the range −20° C. to 10°C. may be preferred.

The fluorine gas employed in the process according to the present invention is preferably diluted before use by mixing with an inert gas such as nitrogen or helium. The concentration of fluorine is preferably from 1% to 50% by volume, more preferably from 2% to 25% by volume, especially from 5% to 15% by volume.

The ratio of fluorine to the reactant compound of formula (2) may be varied within wide limits although it is preferred that the molar ratio of fluorine to compound of formula (2) is in the range of from 4:1 to 15:1 depending on fluorine efficiency in the particular reaction involved.

The method according to the present invention surprising and beneficially offers a convenient novel route to the preparation of organic sulphur pentafluoride compounds of formula (1). Low operating temperatures may advantageously be employed. The use of expensive fluorinating agents such as silver difluoride is avoided. Silver difluoride, for example, has to be regenerated from silver fluoride using elemental fluoride.

All of the fluorine (5 equivalents) required in the conversion of the material of formula (2) into product of formula (1) can be used in the reaction.

For example, we have found that arylsulphur pentafluorides can be prepared in good yields by the direct fluorination of aryl disulphides using elemental fluorine at low to ambient temperatures in suitably inert anhydrous solvents such as acetonitrile. The reaction proceeds as follows:

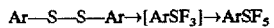

$$Ar—S—S—Ar \rightarrow [ArSF_3] \rightarrow ArSF_5$$

wherein each Ar represents an aryl group. This eliminates the use of silver (II) fluoride which itself has to be regenerated from silver (I) fluoride using elemental fluorine. The reaction proceeds via the highly reactive arylsulphur trifluoride which is quite stable under anhydrous conditions in suitably inert solvents in an inert atmosphere such as nitrogen. Fluorine diluted in nitrogen may be bubbled through a slurry of the aryl disulphide in anhydrous, preferably nitrogen purged acetonitrile at a temperature of −5° C. to −15° C. A virtually colourless solution is formed when all of the starting material has been converted to the intermediate arylsulphur trifluoride. This is subsequently converted to the arylsulphur pentafluoride product by further passage of fluorine.

3

The product of the reaction of the method according to the present invention can be easily treated by solvent removal followed by distillation to separate the compound of formula (2). Any unreacted organic sulphur-trifluoride intermediate can be removed by hydrolysis to form sulphinyl fluoride and subsequent removal by base washing of the crude reaction product.

The reaction may be conveniently monitored eg by nmr or HPLC analysis to detect completion.

Embodiments of the present invention will now be described by way of example only with reference to the following Examples:

EXAMPLE 1
4-Nitrophenylsulphurpentafluoride a) From bis(4-nitrophenyl)disulphide in acetonitrile Bis(4-nitrophenyl)disulphide (12.33 g, 40 mmol) (85% technical grade) was suspended in acetonitrile (200 ml) and cooled to ca. −7.0° C. whilst purging with nitrogen. Fluorine (19.82 g, 52.18 mmol, 13.1 molar equivalents) diluted to 10% in nitrogen was then bubbled through the suspension at −7.6° to −4.5° C. for 24 hours. The solvent was removed from the pale yellow solution to give a dark red oily liquid (21.9 g) which was dissolved in dichloromethane (200 ml) and washed with 10% aqueous sodium hydroxide solution (2×30 ml) followed by water (2×30 ml). After drying over anhydrous magnesium sulphate, the solvent was removed to give a dark red liquid (5.2 g) which was purified further by vacuum distillation to give a pale yellow liquid/low melting solid, 4-Nitrophenylsulphurpentafluoride (8.1 gm 41%) which was shown to be >95% pure by GC/MS [M$^+$ 249]and n.m.r. analysis [(CDCl$_3$) F-19 n.m.r. +76.5 ppm (pentet), +57.9 ppm (doublet), J$^{FF}$ 155Hz]; H-1 n.m.r. 8.37, 8.00 ppm].

b) From bis(4-nitrophenyl)disulphide in chloroform

Bis(4-nitrophenyl)disulphide (40.0 g, 130 mmoles) was suspended in chloroform (200 ml) by vigorous stirring within a refrigerated tubular glass reaction vessel. The mixture was maintained at a temperature of −12° C. throughout the stirring. Fluorine gas (12.2 molar equivalents) diluted with nitrogen (9% fluorine) was bubbled then through the mixture over a period of 633 minutes. The reactor contents were poured into water, extracted into dichloromethane solution; and dried using (MgSO$_4$). The solvent was removed under reduced pressure, yielding an oil that was then steam distilled. The resulting distillate was analysed and shown to contain 4-Nitrophenylsulphurpentafluoride (78% by G.C., overall yield 23%). Tar (35.7 g) was recovered from the distillation residues.

c) From 4-nitrothiophenol

4-Nitrothiophenol (1.04 g, 6.7 moles) was mixed with anhydrous acetonitrile (50 ml) in a 250 ml round bottomed flask. The mixture was maintained at a temperature of ca−5° C. Fluorine gas (8.6 molar equivalents) was diluted with nitrogen containing (10% fluorine) and was bubbled through the mixture over the course of 95 minutes. After workup, 4-Nitrophenylsulphurpentafluoride was obtained (28% yield).

d) From methyl 4-nitrophenylsulphide

Methyl 4-nitrophenylsulphide (0.35 g, 2.1 mmoles) was mixed with anhydrous acetonitrile (50 ml) in a 100 ml round bottomed flask. The mixture was maintained at a temperature of ca −5° C. Fluorine gas (7.0 molar equivalents) diluted with nitrogen containing (10% fluorine) was bubbled through the mixture over a period of 26 minutes. Fluorine n.m.r. analysis indicated that major products included 4-nitrophenylsulphurtrifluoride and 4Nitrophenylsulphurpentafluoride.

4

EXAMPLE 2
3-Nitrophenylsulphurpentafluoride

Bis(3-Nitrophenyl)disulphide (25.0 g, 81.2 mmoles) was mixed with anhydrous acetonitrile (270 ml) in a refrigerated stirred tubular glass reaction vessel (−10° C.). Fluorine gas (14.5 molar equivalents) diluted with nitrogen (10% fluorine) was bubbled through the mixture over the course of 345 minutes. The resulting solution was poured into water and treated with sodium hydroxide solution until alkaline. The resulting mixture was then extracted three times with dichloromethane, the extracts being combined and dried. After solvent removal the resulting brown oil was steam distilled yielding 18.3 g of a yellow oil. The major component of the mixture was identified as 3-Nitrophenylsulphurpentafluoride (38.5% calculated yield; bpt. 106° C., 2torr) G.C./M.S. [M$^+$ 249] and n.m.r. analysis [(CDCl$_3$) F-19 n.m.r.: +80.5 ppm) (1F, pentet); +62.2 ppm (4F, doublet), J$_{FF}$ 151 Hz). H-1 n.m.r.; 7.74 ppm (1H, singlet); 7.56 ppm (1H, doublet J8.1 Hz); 7.26 ppm (1H, doublet J8.1 Hz); 6.91 ppm (1H, triplet J8.1 Hz)].

EXAMPLE 3
2-Nitrophenylsulphurtrifluoride

2-Nitrophenyldisulphide (1.932 g, 6.27 moles) was mixed with anhydrous acetonitrile (50 ml) and cooled (−2° C.). Fluorine gas (12.0 molar equivalents) diluted with nitrogen (10% fluorine) was bubbled through the mixture over the course of 140 minutes. NMR analysis indicated the principal product to be 2-Nitrophenylsulphurtrifluoride ($^{19}$F n.m.r.: 66 ppm, doublet; −47 ppm, triplet).

EXAMPLE 4
4-(Trifluoromethyl)phenylsulphurpentafluoride 4-(Trifluoromethyl)thiophenol (2.01 g, 11.3 mmoles) was mixed with anhydrous acetonitrile (50 ml) in a 100 ml round bottomed flask. The mixture was maintained at a temperature of ca−10° C. Fluorine gas (6.2 molar equivalents) diluted with nitrogen containing (10% fluorine) was bubbled through the mixture over the course of 112 minutes. The resulting solution was poured into water and treated with sodium hydroxide solution until alkaline. The resulting mixture was then extracted three times with dichloromethane, the extracts being combined and dried. After solvent removal the resulting oil was trap to trap distilled under vacuum. 4-(Trifluoromethyl) phenylsulphurpentafluoride was obtained in the distillate (5% overall yield. G.C./M.S. [M$^+$ 272] and n.m.r. analysis [(CDCl$_3$)F-19 n.m.r. +82.4 ppm (1F, pentet), +62.0 ppm (4F, doublet), −63.2 ppm (3F), J$_{FF}$ 149 Hz); H-1 n.m.r. 7.9, 7.8 ppm].

We claim:

1. A method for the preparation of a pentafluoride having a formula (1) as follows:

$$R^1SF_5 \qquad (1)$$

wherein $R^1$ is selected from the group consisting of aryl, heteroaryl, aliphatic, and alicyclic groups, which comprises the step of reacting a disulphide of formula (2) as follows:

$$R^1-S-S-R^2 \qquad (2)$$

wherein $R^2$ is selected from the group consisting of aryl, heteroaryl, aliphatic, and alicyclic groups, in a substantially inert solvent with elemental fluorine.

2. A method as in claim 1 and wherein $R^1$ and $R^2$ are the same.

3. A method as in claim 1 and wherein the groups $R^1$ and $R^2$ are different, the product $R^1SF_5$ being present as a mixture with a corresponding product $R^2SF_5$.

4. A method as in claim 1 and wherein the group $R^1$ or $R^2$ is a substituted aryl group having from one to five substituents, which are less reactive than the disulphide toward fluorine and which do not react with organic sulphur trifluorides formed during the conversion of compounds of formula (2) to those of formula (1).

5. A method as in claim 1 and wherein the compound of formula (2) is of the form $Ar^1$—S—S—$Ar^1$ wherein each $Ar^1$ is selected from the group consisting of a monocyclic aromatic ring and a bicyclic aromatic ring optionally containing one or more substituents or heteroatoms.

6. A method as in claim 5 and wherein the $Ar^1$ groups are the same.

7. A method as in claim 1 wherein the compound of formula (2) is obtained by oxidation of a thiol of formula (3) as follows:

$$R^1\text{—SH} \tag{3}$$

the thiol of formula (3) being converted into the disulphide of formula (2) by use of fluorine in the reacting step.

8. A method as in claim 1 wherein the compound of formula (2) is contained in an inert solvent which is anhydrous.

9. A method as claimed in claim 1 wherein the reacting step is carried out by passing fluorine gas into a solution comprising the compound of formula (2) and the substantially inert solvent.

10. A method as in claim 9 wherein the fluorine gas is diluted before use by mixing with an inert gas.

* * * * *